United States Patent
Pagoulatos et al.

(10) Patent No.: US 10,964,424 B2
(45) Date of Patent: Mar. 30, 2021

(54) ULTRASOUND IMAGE RECOGNITION SYSTEMS AND METHODS UTILIZING AN ARTIFICIAL INTELLIGENCE NETWORK

(71) Applicant: EchoNous, Inc., Redmond, WA (US)

(72) Inventors: Nikolaos Pagoulatos, Kirkland, WA (US); Ramachandra Pailoor, Woodinville, WA (US); Kevin Goodwin, Kirkland, WA (US)

(73) Assignee: EchoNous, Inc., Redmond, WA (US)

( * ) Notice: Subject to any disclaimer, the term of this patent is extended or adjusted under 35 U.S.C. 154(b) by 349 days.

(21) Appl. No.: 15/454,678

(22) Filed: Mar. 9, 2017

(65) Prior Publication Data

US 2017/0262982 A1 Sep. 14, 2017

Related U.S. Application Data

(60) Provisional application No. 62/313,601, filed on Mar. 25, 2016, provisional application No. 62/305,980, filed on Mar. 9, 2016.

(51) Int. Cl.
*G06T 7/00* (2017.01)
*A61B 8/00* (2006.01)
(Continued)

(52) U.S. Cl.
CPC .............. *G16H 30/20* (2018.01); *A61B 8/46* (2013.01); *A61B 8/461* (2013.01); *A61B 8/469* (2013.01);
(Continued)

(58) Field of Classification Search
CPC ........... A61B 8/46; A61B 8/461; A61B 8/469; A61B 8/5215; A61B 8/5223; A61B 8/565;
(Continued)

(56) References Cited

U.S. PATENT DOCUMENTS 7,092,742 B2 8/2006 Rytivaara et al.
7,092,749 B2 * 8/2006 Fowkes ................... A61B 8/00
600/407

(Continued)

FOREIGN PATENT DOCUMENTS

EP 2 980 714 A1 2/2016
RU 2012 138 466 A 3/2014
(Continued)

*Primary Examiner* — Joanne M Hoffman
*Assistant Examiner* — Alexei Bykhovski
(74) *Attorney, Agent, or Firm* — Seed Intellectual Property Law Group LLP

(57) ABSTRACT

Ultrasound image recognition systems and methods, and artificial intelligence training networks for such systems and methods, are provided. An ultrasound data information system includes an ultrasound image recognition training network that is configured to receive ultrasound training images and to develop ultrasound image knowledge based on the received ultrasound training images. An ultrasound imaging device acquires ultrasound images of a patient, and the device includes an ultrasound image recognition module. The ultrasound image recognition module is configured to receive the ultrasound image knowledge, receive the acquired ultrasound images from the ultrasound imaging device, and determine, based on the ultrasound image knowledge, whether the received ultrasound images represent a clinically desirable view of an organ or whether the clinically desirable views indicate normal function or a particular pathology. The received ultrasound images are transmitted to the ultrasound image recognition training network for further training and development of updated ultrasound image knowledge.

35 Claims, 6 Drawing Sheets

(51) Int. Cl.
*A61B 8/08* (2006.01)
*G06F 3/0484* (2013.01)
*G16H 30/20* (2018.01)
*G06K 9/62* (2006.01)
*G16H 50/20* (2018.01)
*G06K 9/46* (2006.01)
*G16H 30/40* (2018.01)

(52) U.S. Cl.
CPC .......... *A61B 8/5215* (2013.01); *A61B 8/5223* (2013.01); *A61B 8/565* (2013.01); *G06F 3/04842* (2013.01); *G06K 9/4628* (2013.01); *G06K 9/6273* (2013.01); *G06T 7/0012* (2013.01); *G16H 30/40* (2018.01); *G16H 50/20* (2018.01); *G06F 3/04845* (2013.01); *G06K 2209/051* (2013.01); *G06T 2200/24* (2013.01); *G06T 2207/10132* (2013.01)

(58) Field of Classification Search
CPC .. G06F 19/36; G06F 3/04842; G06F 3/04845; G06K 2209/051; G06K 9/4628; G06K 9/6273; G06T 2200/24; G06T 2207/10132; G06T 7/0012; G16H 50/20
See application file for complete search history.

(56) References Cited

U.S. PATENT DOCUMENTS

| | | |
|---|---|---|
| 7,421,140 B2 | 9/2008 | Rottem |
| 7,648,460 B2 | 1/2010 | Simopoulos et al. |
| 7,693,349 B2 | 4/2010 | Gering |
| 9,436,995 B2 | 9/2016 | Beymer et al. |
| 9,668,699 B2 | 6/2017 | Georgescu et al. |
| 9,730,643 B2 | 8/2017 | Georgescu et al. |
| 9,734,430 B2 | 8/2017 | Hu et al. |
| 9,918,701 B2 | 3/2018 | Hedlund et al. |
| 2003/0065260 A1* | 4/2003 | Cheng ................. A61B 8/0833 600/427 |
| 2003/0065265 A1 | 4/2003 | Jackson et al. |
| 2004/0019270 A1 | 1/2004 | Takeuchi |
| 2007/0055153 A1* | 3/2007 | Simopoulos .......... G06F 19/321 600/437 |
| 2008/0086283 A1* | 4/2008 | Yuan .................. G05B 23/0254 702/181 |
| 2009/0074280 A1 | 3/2009 | Lu et al. |
| 2009/0093717 A1 | 4/2009 | Carneiro et al. |
| 2010/0036253 A1* | 2/2010 | Vezina ............... A61B 5/02028 600/453 |
| 2012/0065508 A1 | 3/2012 | Gerard et al. |
| 2012/0116227 A1* | 5/2012 | Suzuki .............. A61B 5/02007 600/443 |
| 2014/0221832 A1 | 8/2014 | El-Zehiry et al. |
| 2015/0164478 A1* | 6/2015 | Jung .................. G01S 7/52063 600/443 |
| 2015/0238148 A1 | 8/2015 | Georgescu et al. |
| 2016/0038117 A1* | 2/2016 | Tamada ................. A61B 8/04 600/438 |
| 2016/0038121 A1 | 2/2016 | Waechter-Stehle et al. |
| 2016/0113630 A1 | 4/2016 | Chang et al. |
| 2018/0140282 A1 | 5/2018 | Toyomura et al. |
| 2018/0330518 A1 | 11/2018 | Choi |
| 2018/0333104 A1 | 11/2018 | Sitek |

FOREIGN PATENT DOCUMENTS

| | | |
|---|---|---|
| RU | 2 589 625 C2 | 7/2016 |
| RU | 2 596 991 C2 | 9/2016 |
| WO | 2006/034366 A1 | 3/2006 |
| WO | 2015/087218 A1 | 6/2015 |
| WO | 2016/001784 A1 | 1/2016 |
| WO | 2017/009812 A1 | 1/2017 |

* cited by examiner

ULTRASOUND IMAGE RECOGNITION SYSTEMS AND METHODS UTILIZING AN ARTIFICIAL INTELLIGENCE NETWORK

BACKGROUND

Technical Field

This disclosure generally relates to ultrasound imaging systems and methods and, more particularly, to artificial intelligence based networks for ultrasound imaging and evaluation of ultrasound images, and systems and methods for determining whether acquired ultrasound images represent a clinically desirable view of one or more organs in a patient.

Description of the Related Art

Ultrasound imaging is typically performed in a clinical setting, by trained ultrasound experts. For diagnostic ultrasound imaging, particular views of an organ or other tissue or body feature (such as fluids, bones, joints or the like) are clinically significant. Such views may be prescribed by clinical standards as views that should be captured by the ultrasound technician, depending on the target organ, diagnostic purpose or the like. Ultrasound technicians generally require specialized training to properly operate ultrasound imaging equipment, and to recognize when an acquired image or view of an organ or other tissue or body feature of a patient adequately represents a clinically desirable view. Nonetheless, ultrasound images captured by an ultrasound technician are typically reviewed by a physician to determine whether the captured images sufficiently represent the clinically desirable or standard views.

While conventional ultrasound imaging systems may be suitable for most patients in a hospital or similar clinical setting, such systems require significant training to operate and to adequately capture clinically desirable views. This adds to the overall cost of such ultrasound imaging and further limits the availability of ultrasound imaging to patients, as only well-trained professionals can properly operate conventional ultrasound imaging devices.

BRIEF SUMMARY

The present disclosure provides ultrasound systems and methods that facilitate ultrasound image recognition. In particular, the ultrasound systems and methods are operable to determine whether ultrasound images acquired by an ultrasound imaging device correspond to known, clinically desirable views of one or more organs or tissues or body features in a patient. Artificial intelligence approaches are employed in an ultrasound image recognition module to make such determinations about ultrasound images captured by an ultrasound imaging device.

In one embodiment, an ultrasound system is provided that includes an ultrasound imaging device and an ultrasound image recognition module. The ultrasound imaging device is configured to acquire ultrasound images of a patient. The ultrasound image recognition module is configured to receive the acquired ultrasound images from the ultrasound imaging device and to determine whether the received ultrasound images represent a clinically desirable view of an organ or other body feature. Positive or negative feedback may then be provided to the user to indicate whether or not a clinically desirable view has been captured, such as through a visual or audible cue. To assist the system in determining whether a clinically desirable view has been captured, the user may identify, before or during the image capture process, the particular image perspective or view the user desires to capture, which input the system then can use to assist in identifying whether the desired view in fact has been captured.

In another embodiment, a method is provided that includes acquiring, by an ultrasound imaging device, one or more ultrasound images of a patient; transmitting the acquired ultrasound images of the patient to an ultrasound image recognition module; and determining, by the ultrasound image recognition module, whether the acquired ultrasound images represent a clinically desirable view of an organ or other body feature.

In another embodiment, an ultrasound system is provided that includes an ultrasound imaging device configured to acquire ultrasound images of a patient, and ultrasound image recognition means for determining whether the acquired ultrasound images represent a clinically desirable view of an organ or other body feature.

The present disclosure further provides ultrasound data information systems and methods that facilitate ultrasound image recognition for the purposes of ultrasound image acquisition and interpretation. In particular, the ultrasound data information systems and methods are operable to determine whether, in the context of image acquisition, ultrasound images acquired by an ultrasound imaging device correspond to known, clinically desirable views of one or more organs or tissues or body features in a patient, or in the context of image interpretation, whether ultrasound images acquired by an ultrasound imaging device indicate certain pathologies or normal function. Artificial intelligence approaches are employed in a central artificial intelligence (AI) ultrasound image recognition training network, which is trained to recognize and/or make determinations regarding ultrasound images of a patient. The AI training network and/or the knowledge developed by the AI training network may be provided to, and implemented by, a number of ultrasound imaging devices that may be located anywhere. Utilizing the ultrasound image knowledge developed by the AI training network, the ultrasound imaging devices may thus acquire images of a patient and determine, for example, whether the acquired images represent one or more of the clinically desirable views. Ultrasound images acquired by the ultrasound imaging devices may then be transmitted back to the AI training network, as training input information, thereby further training the AI training network and developing further and/or refined ultrasound image knowledge.

The ultrasound imaging devices may receive periodic updates (e.g., monthly, weekly, daily, or more frequently, etc.) from the AI training network, thus receiving the most recently developed ultrasound image knowledge stored in the AI training network with each update.

In at least one embodiment, an ultrasound data information system is provided that includes an ultrasound image recognition training network, stored at least partially on a computer device having one or more processors. The ultrasound image recognition training network is configured to receive ultrasound training images and develop ultrasound image knowledge based on the received ultrasound training images. The ultrasound data information system further includes an ultrasound imaging device configured to acquire ultrasound images of a patient, and an ultrasound image recognition module within the ultrasound imaging device. The ultrasound image recognition module is configured to receive the ultrasound image knowledge, receive the acquired ultrasound images from the ultrasound imaging device, and determine, based on the ultrasound image knowledge, whether the received ultrasound images represent a clinically desirable view of an organ or a certain pathology.

In another embodiment, the present disclosure provides a method that includes receiving, by an ultrasound image recognition training network, ultrasound training images. The method further includes generating, by the ultrasound image recognition training network, ultrasound image knowledge based on the received ultrasound training images, and transmitting the ultrasound image knowledge to an ultrasound imaging device that is separate from and located remotely from the ultrasound image recognition training network. The ultrasound imaging device may thus acquire ultrasound images of a patient, and determine, based on the ultrasound image knowledge, whether the acquired ultrasound images represent a clinically desirable view of an organ.

DETAILED DESCRIPTION

Figure 1:
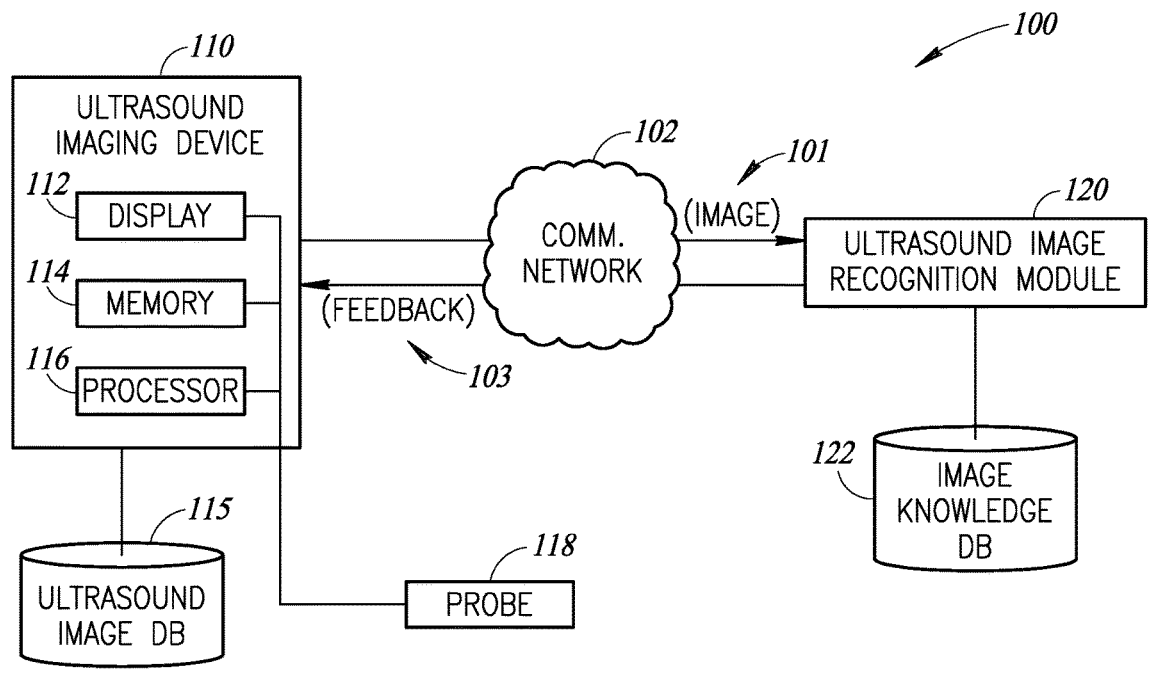
FIG. 1 is a block diagram illustrating an ultrasound image recognition system, in accordance with one or more embodiments of the disclosure.

The present disclosure provides several embodiments of ultrasound image recognition systems and methods. The systems and methods provided herein may be particularly useful for ultrasound imaging performed by novice ultrasound technicians and/or for ultrasound imaging utilizing a handheld or mobile ultrasound imaging device which may be deployed in a non-traditional clinical setting. Utilizing artificial intelligence approaches, the systems and methods provided herein are capable of determining whether acquired ultrasound images accurately depict or represent a desired view of a patient's organ or other tissue, feature or region of interest in a patient. These systems may also then provide feedback to a user to indicate whether or not a desired view of a patient's organ or other tissue or feature has been captured. Alternatively, or in addition, these systems may accept input from a user regarding the particular view of a patient's organ the user desires to capture. In addition, the system may guide the user to attempt to capture one or more particular views of particular anatomy in order, and confirm for the user whether or not one or more of the desired views has been captured.

The present disclosure further provides several embodiments of artificial intelligence network systems and methods for ultrasound imaging. The artificial intelligence systems and methods provided herein may be particularly useful for ultrasound imaging performed by ultrasound technicians at all skill levels and/or for ultrasound imaging utilizing a handheld or mobile ultrasound imaging device which may be deployed in a non-traditional clinical setting. Utilizing artificial intelligence approaches, the systems and methods provided herein are capable of determining whether (i) acquired ultrasound images accurately or substantially accurately depict or represent, or do not accurately or substantially accurately depict or represent, a desired view of a structure and/or anatomy including, for example, a patient's organ or other tissue, feature or region of interest in a patient, and (ii) whether acquired images representing clinically desired views of anatomy indicate normal function or a particular pathology. For example, based on acquired ultrasound images determined to substantially accurately depict or represent a particular view of a heart, the artificial intelligence approaches may further indicate a particular problem with the mitral valves in the heart.

An artificial intelligence ultrasound image recognition training network ("AI training network") may be a cloud-based or distributed computing network, and may be accessible to a large number of ultrasound imaging devices. The AI training network may be trained using a large number of ultrasound images representing known or clinically determined views, and within these views ultrasound images may represent normal or pathological function. Through a training process, the parameters of the AI training network are optimized for recognition of a variety of views of structures, such as organs, tissue or any other region of interest in a patient and for a variety of normal and pathological conditions. The AI training network and/or the network parameters (e.g., any knowledge learned by the AI training network via the training process) may be downloaded and implemented by the ultrasound imaging devices in order to recognize, interpret and/or make determinations with respect to acquired ultrasound images. Accordingly, the ultrasound imaging devices need not be individually trained (which is a computationally intensive process). Ultrasound images acquired by the ultrasound imaging devices may be transmitted back to the AI training network, as training input to further train the AI training network.

FIG. 1 illustrates a block diagram of an ultrasound system 100, in accordance with embodiments of the present disclosure. As shown in FIG. 1, the ultrasound system 100 includes an ultrasound imaging device 110, a communications network 102, an ultrasound image recognition module 120 and an image knowledge database 122. Each of these may be incorporated into a single ultrasound device, such as a hand-held or portable device, or may constitute multiple devices operatively linked or linkable to one another.

The ultrasound imaging device 110 is any ultrasound device operable to acquire ultrasound images of a patient, and may be, for example, a handheld ultrasound imaging device. The ultrasound imaging device 110 may include a display 112, memory 114, one or more processors 116. The ultrasound imaging device 110 is operatively coupled to an ultrasound probe 118.

The memory 114 may be or include any computer-readable storage medium, including, for example, read-only memory (ROM), random access memory (RAM), flash memory, hard disk drive, optical storage device, magnetic storage device, electrically erasable programmable read-only memory (EEPROM), organic storage media, or the like.

The processor 116 may be any computer processor operable to execute instructions (e.g., stored in memory 114) to perform the functions of the ultrasound imaging device 110 as described herein.

The ultrasound probe 118 is driven by the ultrasound imaging device 110 to transmit signals toward a target region in a patient, and to receive echo signals returning from the target region in response to the transmitted signals. In operation, a user of the ultrasound device 110 may hold the probe 118 against a patient's body at a position and angle to acquire a desired ultrasound image. The signals received by the probe (i.e., the echo signals) are communicated to the ultrasound imaging device 110 and may form, or be processed to form, an ultrasound image of the target region of the patient. Further, the ultrasound images may be provided to the display 112, which may display the ultrasound images and/or any other relevant information to the user.

The ultrasound images thus acquired by the ultrasound imaging device 110 may be provided to the ultrasound image recognition module 120 via a communications network 102. Ultrasound images from the ultrasound imaging device 110 are provided to the ultrasound image recognition module 120, as shown by reference numeral 101. Communications network 102 may utilize one or more protocols to communicate via one or more physical networks, including local area networks, wireless networks, dedicated lines, intranets, the Internet, and the like.

In one or more embodiments, the ultrasound image recognition module 120 may be provided within the ultrasound imaging device 110, or a local copy of the ultrasound image recognition module 120 and/or ultrasound knowledge stored in the image knowledge database 122 may be contained within the ultrasound imaging device 110, with the ultrasound imaging device 110 having access to a remotely located (e.g., stored on one or more server computers, or in the "cloud") ultrasound image recognition module 120, e.g., for receiving updated ultrasound image recognition algorithms and/or knowledge.

The ultrasound image recognition module 120 receives the ultrasound images acquired from the ultrasound imaging device 110, and determines whether one or more of the received ultrasound images represent a clinically desirable view of an organ or other aspect, region or feature of the patient. The ultrasound image recognition module 120 may be implemented by any computationally intelligent system that employs artificial intelligence, drawing from an image knowledge database 122, to determine whether received ultrasound images represent a clinically desirable view. Some or all of the determinations described herein that are made by the ultrasound image recognition module may be performed automatically by the ultrasound image recognition module 120, for example, in response to receiving the acquired ultrasound images.

"Artificial intelligence" is used herein to broadly describe any computationally intelligent systems and methods that can learn knowledge (e.g., based on training data), and use such learned knowledge to adapt its approaches for solving one or more problems. Artificially intelligent machines may employ, for example, neural network, deep learning, convolutional neural network, and Bayesian program learning techniques to solve problems such as image recognition. Further, artificial intelligence may include any one or combination of the following computational techniques: constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing one or more computationally intelligent techniques, the ultrasound image recognition module 120 may learn to adapt to an unknown and/or changing environment for better performance.

The image knowledge database 122 may include a variety of information facilitating image analysis, with respect to received ultrasound images, by the ultrasound image recognition module 120. In particular, the image knowledge database 122 may contain information relating to various image views of various organs. For example, the image knowledge database 122 may include information associated with clinically standard or desirable views of a heart. The clinically standard views of a heart may include, for example, suprasternal, subcostal, short- and long-axis parasternal, 2-chamber apical, 3-chamber apical, 4-chamber apical and 5-chamber apical views. Additionally, the information associated with clinically standard views may be information associated with a three-dimensional view, a two-dimensional cross section view and/or a set of two-dimensional cross section views. The image knowledge database 122 may be stored in any computer-readable storage medium accessible by the ultrasound image recognition module 120.

The ultrasound image recognition module 120 may include, or otherwise be executed by, a computer processor configured to perform the various functions and operations described herein. For example, the ultrasound image recognition module 120 may be executed by a general purpose computer or a data processor selectively activated or reconfigured by a stored computer program, or may be a specially constructed computing platform for carrying out the features and operations described herein.

Figure 2:
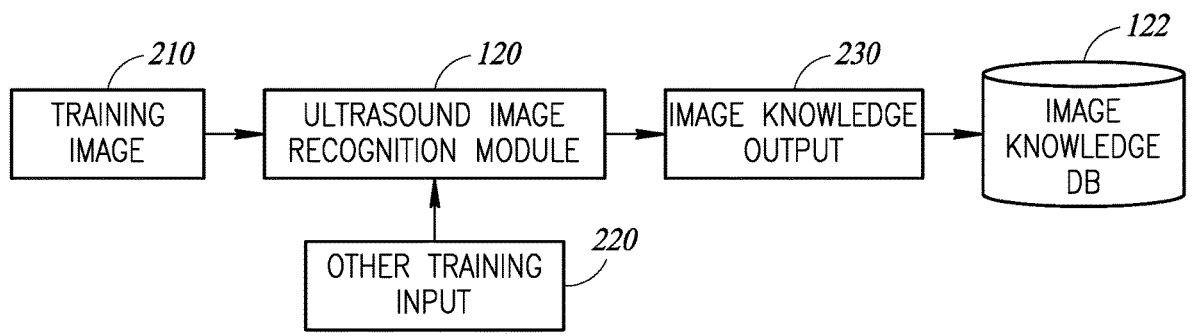
FIG. 2 is a block diagram illustrating training of the ultrasound image recognition module, in accordance with one or more embodiments of the disclosure.

FIG. 2 is a block diagram illustrating training of the ultrasound image recognition module 120, in accordance with one or more embodiments. The ultrasound image recognition module 120 may be trained based on training images 210. Training images 210 may include any ultrasound image information. For example, the training images 210 may include a variety of ultrasound image information associated with known views of an organ, such as the heart. As a further example, the training images 210 may be clinically desirable images of, e.g., suprasternal views of a heart. In such a case, the training images 210 may be ultrasound images which have been pre-determined (e.g., by a physician) as adequately showing a clinically desirable suprasternal view of a heart. Each such training image 210 may have slightly different characteristics (e.g., higher quality images, lower quality images, blurry images, images taken at slightly different angles, and so on), yet each such training image 210 may nonetheless be pre-determined as adequately representing a clinically desirable view of a heart.

Moreover, the training images 210 may include not only image information associated with clinically standard or desirable views, but may further include image information associated with non-clinically desirable views. Accordingly, the ultrasound recognition module 120 may receive, for example, a view of a heart which is not representative of any particular clinically desirable view (e.g., suprasternal, subcostal, short- and long-axis parasternal, 2-chamber apical, 3-chamber apical, 4-chamber apical and 5-chamber apical views). In such a case, the ultrasound recognition module 120 may nonetheless recognize the image as being a view of a heart, and may further recognize the image as being an image somewhere between, for example, a 2-chamber apical view and a 3-chamber apical view. A clinically standard 3-chamber apical view is generally obtainable, for example, by rotating an ultrasound imaging probe about 60° counterclockwise with respect to the 2-chamber apical view. Ultrasound images obtained with the probe at an angle of rotation somewhere between, for example, 5° and 55° counterclockwise with respect to the 2-chamber apical view may be determined as not representing a clinically desirable view of a heart. However, the ultrasound image recognition module 120 may be trained with training images 210 showing a variety of known, but non-clinically desirable, views of a heart (such as views somewhere between the 2-chamber apical and the 3-chamber apical views), and thus may recognize such views (e.g., the ultrasound image recognition module 120 may recognize a view as representing a 35° counterclockwise rotation of the probe 118 with respect to the 2-chamber apical view).

Other training input 220 may further be provided to the ultrasound image recognition module 120 for training. The other training input 220 may include, for example, manually-entered input to adjust or otherwise manage the image recognition model developed in the image recognition module 120 through the training process.

Using training images 210, the ultrasound image recognition module 120 may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

Figure 3:
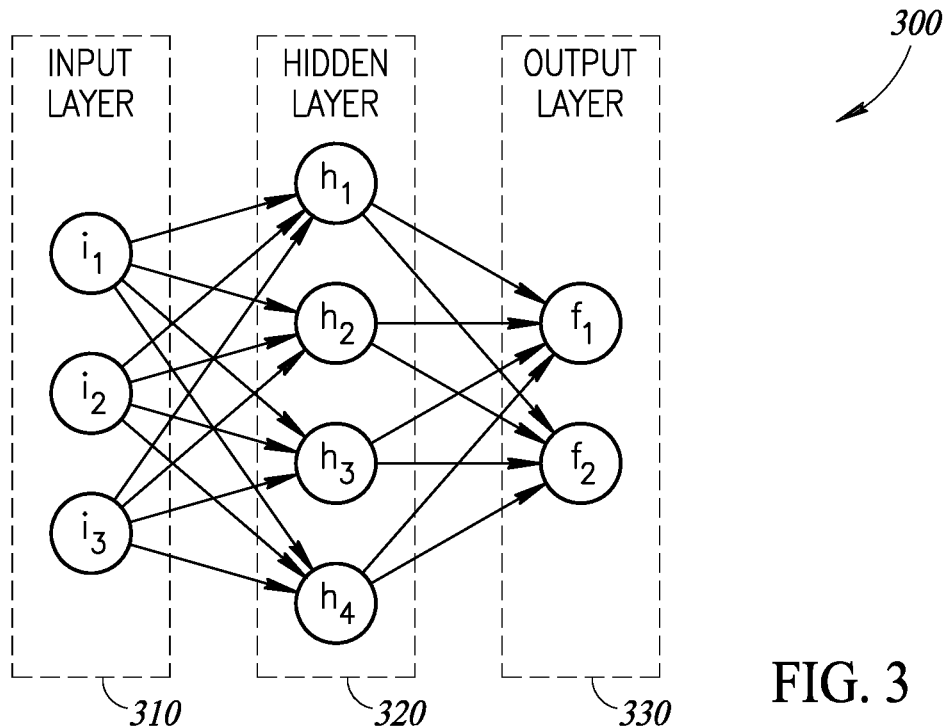
FIG. 3 is a block diagram illustrating a neural network, which may be implemented by the ultrasound image recognition module, in accordance with one or more embodiments of the disclosure.

The back-propagation learning algorithm is a common method of training artificial neural networks (and may be employed, for example, with the artificial neural network 300 shown in FIG. 3). Back-propagation generally includes two phases: propagation and weight update. In the propagation phase, a training pattern's input is forward propagated through the neural network in order to generate the propagation's output activations. Then, the propagation's output activations are backward propagated through the neural network using the training pattern target in order to generate deltas (i.e., the difference between the input and output values) of all output and hidden neurons. In the weight update phase, for each weight-synapse the following steps are generally performed: 1. Multiply its output delta and input activation to get the gradient of the weight; 2. Subtract a ratio (percentage) of the gradient from the weight. The propagation and weight update phases are repeated as desired until performance of the network is satisfactory.

As a result of the training, the ultrasound image recognition module 120 may learn to modify its behavior in response to the training images 210, and obtain or generate ultrasound image knowledge 230. The ultrasound image knowledge 230 may represent any information upon which the ultrasound image recognition module 120 may determine an appropriate response to new data or situations. In particular, the ultrasound image knowledge 230 represents relationships between ultrasound images and one or more views of an organ (e.g., one or more functions that describe one or more views of an organ based on ultrasound image parameters, coefficients, weighting information, parameters associated with the example neural network shown in FIG. 3 or any such variable). The ultrasound image knowledge 230 may be stored in the ultrasound image knowledge database 122.

Based on the training images 210, the ultrasound image recognition module 120 may learn to modify its behavior, and may apply knowledge contained in the image knowledge database 122 to alter the manner in which it makes determinations with respect to new input, such as, for example, ultrasound image information received from the ultrasound imaging device 110.

FIG. 3 is a block diagram illustrating one example of an artificial neural network 300, which may be implemented by the ultrasound image recognition module 120, in accordance with one or more embodiments. Artificial neural networks (ANNs) are artificial intelligence models that are used to estimate or approximate functions that can depend on a large number of inputs, and which are generally unknown. Such neural networks generally include a system of interconnected "neurons" which exchange information between each other. The connections have numeric weights that can be tuned based on experience, and thus neural networks are adaptive to inputs and are capable of learning.

The artificial neural network 300 shown in FIG. 3 includes three layers: an input layer 310 including input neurons $i_1$ through $i_3$, a hidden layer 320 including hidden layer neurons $h_1$ through $h_4$, and an output layer 330 including output neurons $f_1$ and $f_2$. While the neural network 300 of FIG. 3 is shown having three layers, it should be readily appreciated that additional layers may be included in the neural network 300 as desired to achieve optimal training and performance of the ultrasound image recognition module 120. Similarly, the neurons in each layer are shown for exemplary purposes, and it should be readily understood that each layer may include more, even significantly more, neurons than shown in FIG. 3.

The neural network 300 may be trained by providing training images 210 to the input layer 310. As described with respect to FIG. 2, the training images may include ultrasound image information having a wide variety of known characteristics, including, for example, various organ views, various image qualities or characteristics, various imaging angles, and so on. Through training, the neural network 300 may generate and/or modify the hidden layer 320, which represents weighted connections mapping the training images 210 provided at the input layer 310 to known output information at the output layer 330 (e.g., classification of an image as a subcostal view of a heart, a suprasternal view, etc.). Relationships between neurons of the input layer 310, hidden layer 320 and output layer 330, formed through the training process and which may include weight connection relationships, are generally referred to herein as "ultrasound image knowledge," and may be stored, for example, in the ultrasound image knowledge database 122.

Once the neural network 300 has been sufficiently trained, the neural network 300 may be provided with non-training ultrasound images at the input layer 310 (i.e., ultrasound images taken of a patient utilizing the ultrasound imaging device 110). Utilizing ultrasound image knowledge stored in the ultrasound image knowledge database 122 (which may include, for example, weighted connection information between neurons of the neural network 300), the neural network 300 may make determinations about the received ultrasound image information at the output layer 330. For example, the neural network 300 may determine whether the received ultrasound images represent one or more clinically desirable views of an organ.

The neural network 300 of FIG. 3 is provided as just one example, among various possible implementations of an ultrasound image recognition module 120 that employs artificial intelligence to make determinations with respect to received ultrasound image information. For example, the ultrasound image recognition module 120 may implement any of neural network, deep learning, convolutional neural network, and Bayesian program learning techniques to make determinations with respect to received ultrasound images of a patient.

Moreover, the ultrasound recognition module 120 may be trained, utilizing a variety of training images 210 and/or a variety of sequences of training images 210, to make a variety of determinations relating to received ultrasound image information. For example, the ultrasound recognition module 120 may be trained or otherwise configured to determine whether a received ultrasound image represents one or more clinically standard or desirable views. Further, the ultrasound recognition module 120 may determine whether a received ultrasound image represents a non-clinically desirable view (and may recognize such non-clinically desirable view as a particular view or angle of a particular organ or other tissue within a patient), and may further determine based on a sequence of received ultrasound images whether the images are approaching or moving away from a clinically desirable view of an organ. Based on its recognition of whether the images are approaching or moving away from a clinically desirable view of the organ, and/or on its recognition of the actual image captured, the system may then be configured to provide feedback to the user to assist the user in capturing the desired view of the organ, for example, by indicating a direction in which the user may wish to move the probe and/or an angle of rotation or orientation in which the user may wish to angle the probe.

For example, as discussed above, the ultrasound image recognition module 120 may be trained with training images 210 showing a variety of known, but non-clinically desirable, views of a heart (such as views somewhere between the 2-chamber apical and the 3-chamber apical views), and thus may recognize such views (e.g., the ultrasound image recognition module 120 may recognize a view as representing a 35° counterclockwise rotation of the probe 118 with respect to the 2-chamber apical view). Further, the ultrasound image recognition module 120 may be trained with a sequence of recognized, but non-clinically standard or desirable views of a heart. For example, the ultrasound image recognition module 120 may be trained to recognize ultrasound images showing a view of the heart at each degree of counterclockwise rotation between 0° and 60° with respect to the 2-chamber apical view (i.e., every degree between the 2-chamber apical and the 3-chamber apical views). Further, the ultrasound image recognition module 120 may be trained to recognize a sequence of or progression of such non-clinically desirable views toward and/or away from a clinically desirable view (e.g., the training images 210 may include a sequence of ultrasound images representing rotation of the probe 118 from the 2-chamber apical view toward and/or away from the 3-chamber apical view). The ultrasound image recognition module 120 may thus be trained to recognize that received ultrasound images, while not being representative of a particular clinically desired view, may be getting successively closer to (or moving away from) the clinically desired view.

Further, the ultrasound image recognition module 120 may be trained such that the ultrasound image recognition module 120 may determine whether received ultrasound images represent any of a plurality of clinically desirable views of an organ. Such clinically desirable views of an organ may include, for example, suprasternal, subcostal, short- and long-axis parasternal, 2-chamber apical, 3-chamber apical, 4-chamber apical and 5-chamber apical views of a heart.

Referring again to FIG. 1, the ultrasound image recognition module 120 may provide a feedback signal (indicated by reference numeral 103) to the ultrasound imaging device 110, as described in further detail below. The feedback signal 103 may be provided in response to a determination made by the ultrasound image recognition module 120 with respect to a received ultrasound image.

Figure 4:
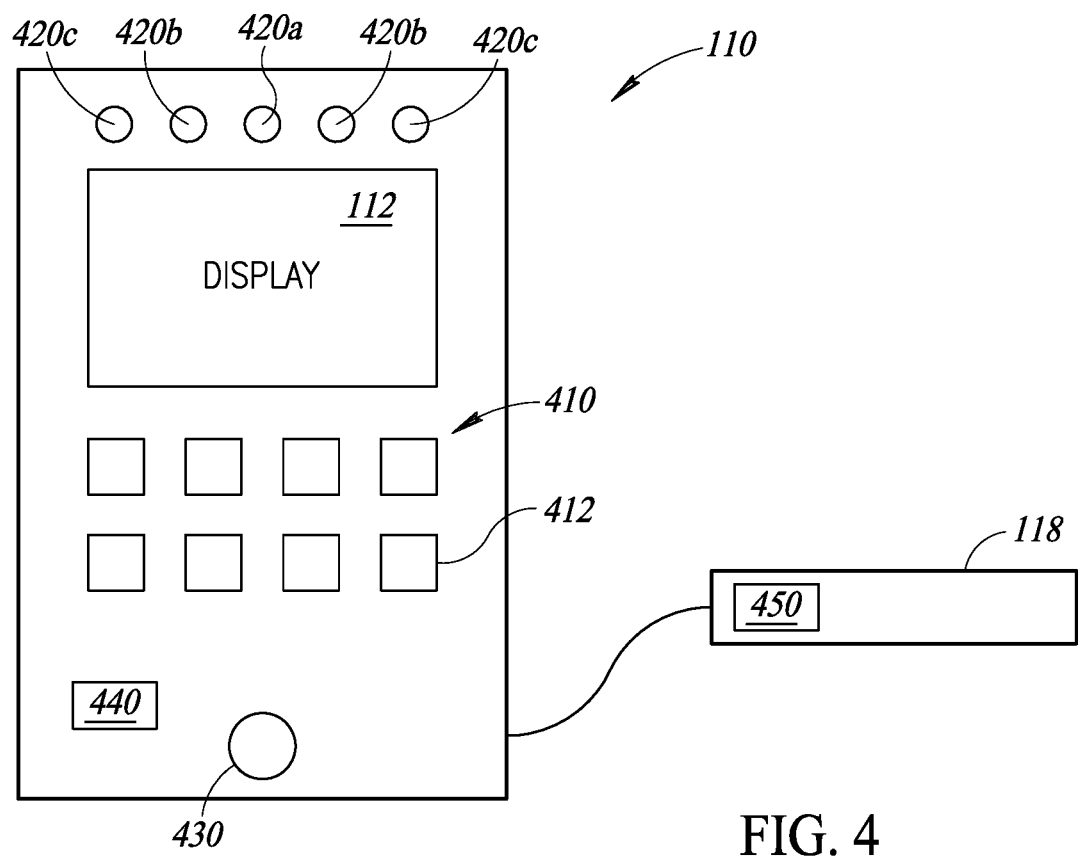
FIG. 4 is a schematic illustration of an ultrasound imaging device, in accordance with one or more embodiments of the disclosure.

FIG. 4 schematically illustrates an ultrasound imaging device 110, in accordance with one or more embodiments. The ultrasound imaging device 110 may include a display 112, a user interface 410 including one or more input elements 412, one or more visual feedback elements 420, an audible feedback element 430 and/or a haptic feedback element 440.

The user interface 410 allows a user to control or otherwise communicate with the ultrasound imaging device 110. Various types of user input may be provided, for example, via the user input elements 412, which may be buttons or similar user input elements. Additionally or alternatively, the display 112 may be a touchscreen display, and user input may be received via the display 112. Using the ultrasound imaging device 110, a user may select (e.g., via the input elements 412 and/or display 112) or otherwise input a desired view of an organ that is to be imaged in a patient. For example, a user may select one view (e.g., a subcostal view of a heart) from among a plurality of clinically desirable views that are stored in the ultrasound imaging device 110 and presented to the user. The ultrasound imaging device 110 may communicate the selected view to the ultrasound image recognition module 120, and the ultrasound image recognition module 120 may thus be configured to determine whether received ultrasound images represent the selected view. That is, the ultrasound image recognition module 120 may access the appropriate ultrasound image knowledge (e.g., knowledge, rules or relations associated with a subcostal view of a heart) in the image knowledge database 122 such that received ultrasound images may be compared with, or processed by, knowledge corresponding to the selected view. Alternatively, the user may select a mode of operation in which the system guides the user through capture of one of more of a series of standard views of an organ, such as a heart as described above. In such a mode, the system would first select a desired view of the organ to be imaged, and then confirm for the user when the desired image had been captured and/or guide the user towards the desired view based on the initial image capture. The system would then repeat this process, in series, for each of the desired standard views of the organ to be imaged. Alternatively, the system could operate in such a way to compare any captured image against each of the images to be captured and confirm when one or more of the desired standard views had been captured, without first indicating which view was to be captured first.

The visual feedback elements 420 may be any element that can provide a visual indication to a user of the ultrasound imaging device 110, and may be, for example, one or more lights, colors, shapes, icons or the like, whether static or moving. The audible feedback element 430 may be any element capable of producing an audible indication to a user of the ultrasound imaging device 110, and may be, for example, a speaker for producing various tones or sounds associated with lack of correspondence and correspondence between the captured image and the image desired to be captured. Similarly, the haptic feedback element 440 may be any element capable of providing a haptic effect to a user of the ultrasound imaging device 110, and may be, for example, a vibration device.

Feedback signals 103 provided by the ultrasound image recognition module 120 may indicate any of a variety of determinations made by the ultrasound image recognition module 120 regarding ultrasound images received from the ultrasound imaging device 110.

For example, the ultrasound image recognition module 120 may provide a feedback signal 103 indicating that a current or most recently received ultrasound image represents a clinically desirable view of the organ (e.g., the selected clinically desirable view). In a further example, the ultrasound image recognition module 120 may determine whether the received ultrasound images are sequentially approaching or moving away from a clinically desirable view of an organ, and provides a feedback signal 103 that indicates whether the received ultrasound images are sequentially approaching or moving away from the clinically desirable view of the organ. This feedback signal could include a visual or audible command to instruct the user to move or angle the probe in a certain way, or an icon, such as a straight or curved arrow(s), indicating the direction and/or angle of movement required of the probe in order to better approach the desired image of the organ.

The ultrasound imaging device 110 receives the feedback signal 103, and in response, may activate one or more feedback elements (i.e., visual feedback elements 420, audible feedback element 430 and/or haptic feedback element 440) to provide a feedback effect to a user of the ultrasound imaging device 110. For example, the feedback signal 103 may indicate that the current or most recently received ultrasound image represents a clinically desirable view of an organ. In such a case, the feedback effect provided by the ultrasound imaging device 110 may include flashing a green light 420a of the visual feedback element 420, an audible tone or beep from the audible feedback element 430 and/or a vibrational pulse provided by the haptic feedback element 440. The flashing green light 420a, audible tone and/or vibrational pulse indicates to the user that the desired view has been obtained, and the user may thus retain the ultrasound image of the desired view (e.g., utilizing one or more of the user input elements 412) and store the image in an ultrasound image database 115.

Additionally or alternatively, upon determining that a clinically desirable view of an organ is represented in a received ultrasound image, the ultrasound image recognition module 120 may cause (e.g., by a feedback signal 103) the ultrasound imaging device 110 to automatically retain and store the ultrasound image in the ultrasound image database 115. A table may also be displayed with appropriate indications next to each desired type of image, to indicate whether the user had already captured the desired image or whether the desired image remains to be captured for the particular patient being imaged.

In embodiments where a feedback signal 103 indicates that the received ultrasound images are sequentially approaching or moving away from the clinically desirable view of the organ, the ultrasound imaging device 110 may communicate this to the user, for example, by providing a changing feedback effect, such as an audible tone having an increasing (or decreasing) frequency as the received ultrasound images are approaching (or moving away from) the clinically desired view, a series of vibrational pulses having an increasing (or decreasing) intensity as the received ultrasound images are approaching (or moving away from) the clinically desired view, and/or illuminating a different color or position of lights as the received ultrasound image are approaches or moving away from the clinically desired view (e.g., illuminating red outer lights 420c, then yellow intermediate lights 420b, then green center light 420a as the received ultrasound images approach the clinically desired view).

The probe 118, which is operatively coupled with the ultrasound imaging device 110, may include one or more motion sensors 450, which may be any motion sensors, including, for example, accelerometers, gyroscopes, or the like. Accordingly, the ultrasound imaging device 110 may determine a position and/or motion of the probe 118. In particular, the ultrasound imaging device 110 may determine a position and/or motion of the probe 118 with respect to one or more known points on a patient. For example, a user may position the probe 118 in a known orientation (e.g., substantially normal to the patient's skin) at a known point on the patient (e.g., a particular point on the patient's chest), and the ultrasound imaging device 110 may capture (e.g., via user input elements 412) this position as a reference or initialization point. The ultrasound imaging device 110 may thus determine its position with respect to the known reference point utilizing any known positioning algorithms, including, for example, inertial navigation techniques. Similarly, the ultrasound image recognition module 120 may determine, for example, that the received ultrasound images are moving away from a clinically desirable view (as described herein), and may recommend a movement (e.g., via feedback signal 103) of the probe 118, with respect to the known point on the patient, in order to acquire the clinically desirable view. For example, the ultrasound image recognition module 120 may determine, for example, that the received ultrasound images represent successive views of a heart associated with 45°, 40°, then 35° of counterclockwise rotation with respect to the 2-chamber apical view. The clinically desirable view may be, for example, a 3-chamber apical view, which may be obtainable by rotating the probe 118 about 60° with respect to the 2-chamber apical view. Accordingly, the ultrasound image recognition module 120 may determine that the received ultrasound images are moving away from the clinically desirable view, and may further recommend, for example, that the user rotate the probe 118 about 25° (as the most recent view may represent a 35° counterclockwise rotation with respect to the 2-chamber apical view, an additional 25° counterclockwise rotation should result in the desired 3-chamber apical view) in a counterclockwise direction in order to obtain the 3-chamber apical view.

While the ultrasound image recognition module 120 has been described herein as being separate from the ultrasound imaging device 110, and accessible via the communications network 102, it should be readily appreciated that the ultrasound image recognition module 120 may be included within the ultrasound imaging device 110. That is, the ultrasound image recognition module 120 (either the image recognition module 120 itself, or a local copy of a remotely located image recognition module 120) may be contained within the ultrasound imaging device 110, and may be stored, for example, in memory 114 and the features and/or functionality of the ultrasound image recognition module 120 may be executed or otherwise implemented by the processor 116.

Figure 5:
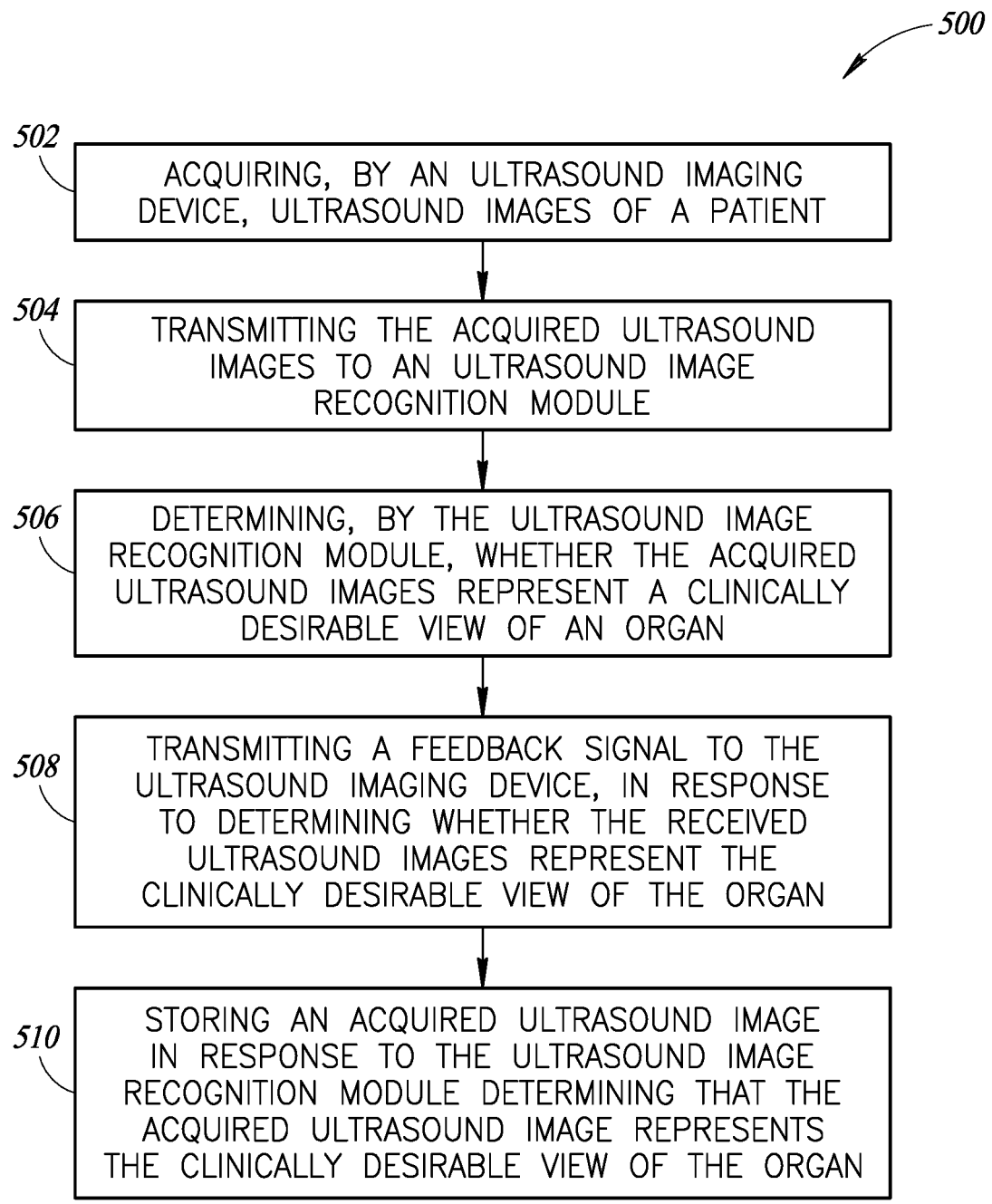
FIG. 5 is a flowchart illustrating an ultrasound image recognition method, in accordance with one or more embodiments of the disclosure.

FIG. 5 is a flowchart illustrating an ultrasound image recognition method 500, in accordance with one or more embodiments. At block 502, the method 500 includes acquiring, by an ultrasound imaging device 110, ultrasound images of a patient. The acquired ultrasound images may include, for example, a view of an organ in the patient.

At block 504, the method 500 includes transmitting the acquired ultrasound images to an ultrasound image recognition module 120. The acquired ultrasound images may be transmitted via a communications network 102, or alternatively, the ultrasound image recognition module 120 may be contained within the ultrasound imaging device 110, and the acquired ultrasound images may be transmitted via a hard-wired connection.

At block 506, the method 500 includes determining, by the ultrasound image recognition module 120, whether the acquired ultrasound images represent a clinically desirable view of an organ. The ultrasound image recognition module 120 may employ any artificial intelligence methodologies to facilitate the determination, as shown and described, for example, in FIGS. 2 and 3.

At block 508, the method 500 may further include transmitting a feedback signal 103 to the ultrasound imaging device 110, in response to determining whether the received ultrasound images represent the clinically desirable view of the organ. The feedback signal 103 may communicate a variety of potential messages to the ultrasound imaging device 110. For example, the feedback signal 103 may indicate that an acquired ultrasound image represents the clinically desirable view, does not represent the clinically desirable view, and/or the images are sequentially approaching or moving away from the clinically desirable view.

At block 510, the method 100 may further include storing an acquired ultrasound image in response to the ultrasound image recognition module 120 determining that the acquired ultrasound image represents the clinically desirable view of the organ. In such a case, the acquired ultrasound image may be automatically stored, for example, in the ultrasound image database 115. Additionally or alternatively, a user of the ultrasound imaging device 110 may be prompted to store the acquired ultrasound image, for example, by providing an input to the ultrasound imaging device 110 via the user interface 410.

Figure 6:
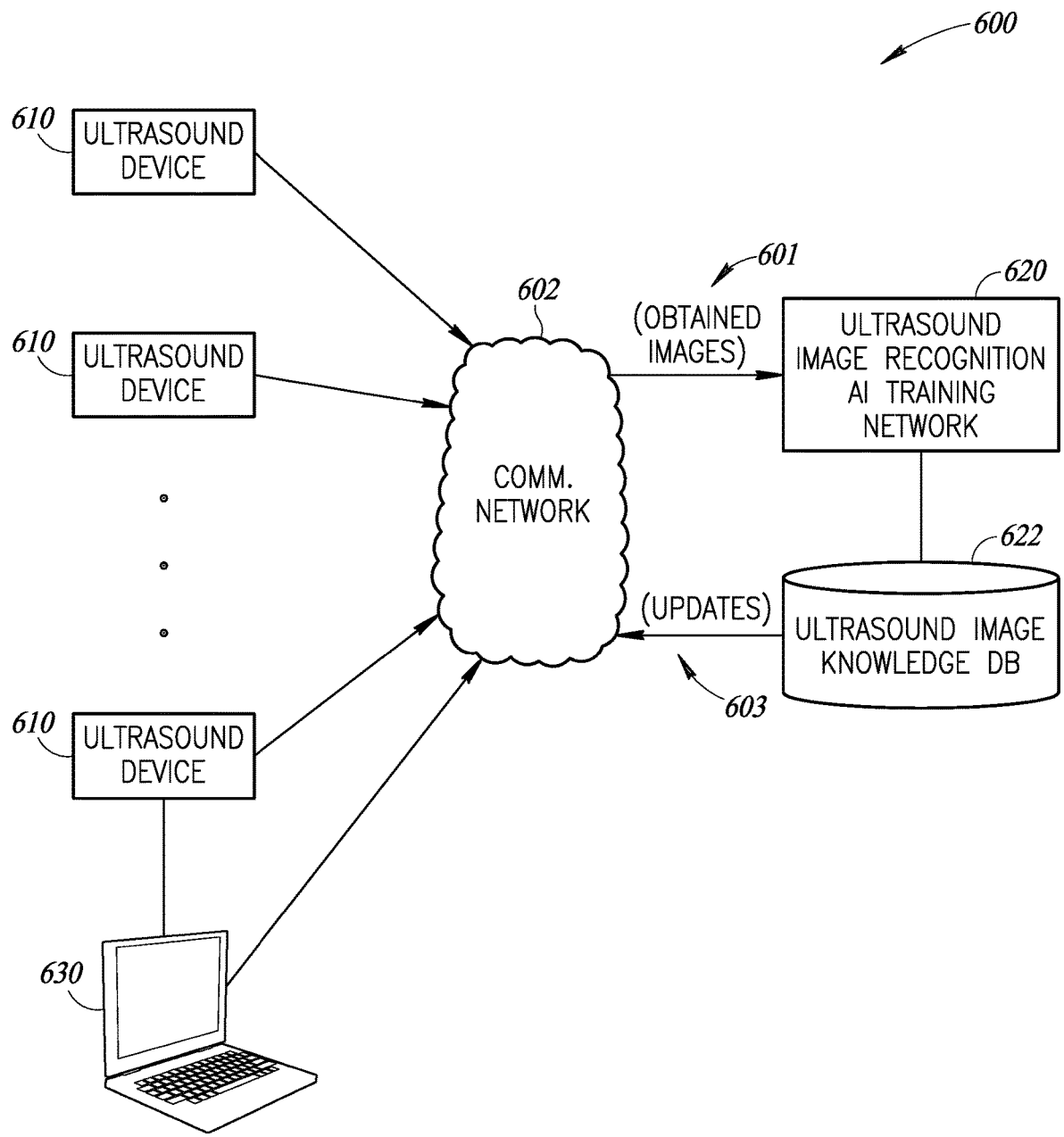
FIG. 6 is a block diagram illustrating an ultrasound data information system in accordance with one or more embodiments of the disclosure.

FIG. 6 illustrates a block diagram of an ultrasound data information system 600 in accordance with embodiments of the present disclosure. As shown in FIG. 6, the ultrasound data information system 600 includes a number of ultrasound imaging devices 610, a communications network 602, a cloud-based artificial intelligence (AI) ultrasound image recognition training network 620 (referred to hereinafter as "AI training network 120") and an ultrasound image knowledge database 622. The ultrasound data information system 600 may further include one or more user computer devices 630.

The AI training network 620 is a cloud-based or distributed computing artificial intelligence network that is trained to recognize ultrasound images. In particular, the AI training network 620 may be trained to determine whether received ultrasound images represent a clinically desirable view of an organ or other aspect, region or feature of a patient, or whether the clinically desirable views indicate normal function or a particular pathology. The AI training network 620 may be implemented by any computationally intelligent system that employs artificial intelligence, drawing from training inputs to learn or otherwise generate knowledge (e.g., as stored in the image knowledge database 622), which is utilized to determine whether received ultrasound images represent a clinically desirable view or whether the clinically desirable views indicate normal function or a particular pathology.

Employing one or more computationally intelligent techniques, the AI training network 620 may learn to adapt to an unknown and/or changing environment for better performance.

Through an artificial intelligence training process, the AI training network 620 learns knowledge, which is stored in the image knowledge database 622. The knowledge stored in image knowledge database 622 may include a variety of information facilitating ultrasound image analysis, with respect to received ultrasound images, by the AI training network 620 and/or by an ultrasound image recognition module 621 within the ultrasound imaging devices 610, as will be described in further detail herein. In particular, for example, the image knowledge database 622 may contain information relating to various image views of various organs, and normal and pathological states of various organs. For example, the image knowledge database 622 may include information associated with clinically standard or desirable views of a heart. The clinically standard views of a heart may include, for example, suprasternal, subcostal, short- and long-axis parasternal, 2-chamber apical, 3-chamber apical, 4-chamber apical and 5-chamber apical views. Additionally, the information associated with clinically standard views may be information associated with a three-dimensional view, a two-dimensional cross section view and/or a set of two-dimensional cross section views. Similarly, the image knowledge database 622 may include information associated with normal function of organs, such as a heart, and various pathological conditions of an organ, including for example, cardiac muscle contractility and valve function. The image knowledge database 622 may be stored in any computer-readable storage medium accessible by the AI training network 620.

The AI training network 620 may include, or otherwise be executed by, one or more computer processors configured to perform the various functions and operations described herein. For example, the AI training network 620 may be executed by one or more general purpose computers or data processors selectively activated or configured by a stored computer program, or may be a specially constructed computing platform for carrying out the features and operations described herein. In particular, the AI training network 620 may be a cloud-based or distributed computing artificial intelligence network having a high level of computational capability such that it can receive and process a very large number (e.g., tens of thousands, or more) of training images to generate ultrasound image knowledge. In one or more embodiments, the AI training network 620 may be included within and/or executed in an ultrasound imaging device 610.

The ultrasound imaging devices 610 may be any ultrasound devices operable to acquire ultrasound images of a patient, and may be, for example, handheld ultrasound imaging devices. The ultrasound imaging devices 610 shown in FIG. 6 may be the same, or substantially the same, as the ultrasound imaging devices 110 shown in FIG. 1. In particular, the ultrasound imaging devices 610 may include the same features as discussed above with respect to the ultrasound imaging devices 110 (and shown, for example, in FIGS. 1 through 4), and may further include additional features as discussed below with respect to FIG. 7.

Figure 7:
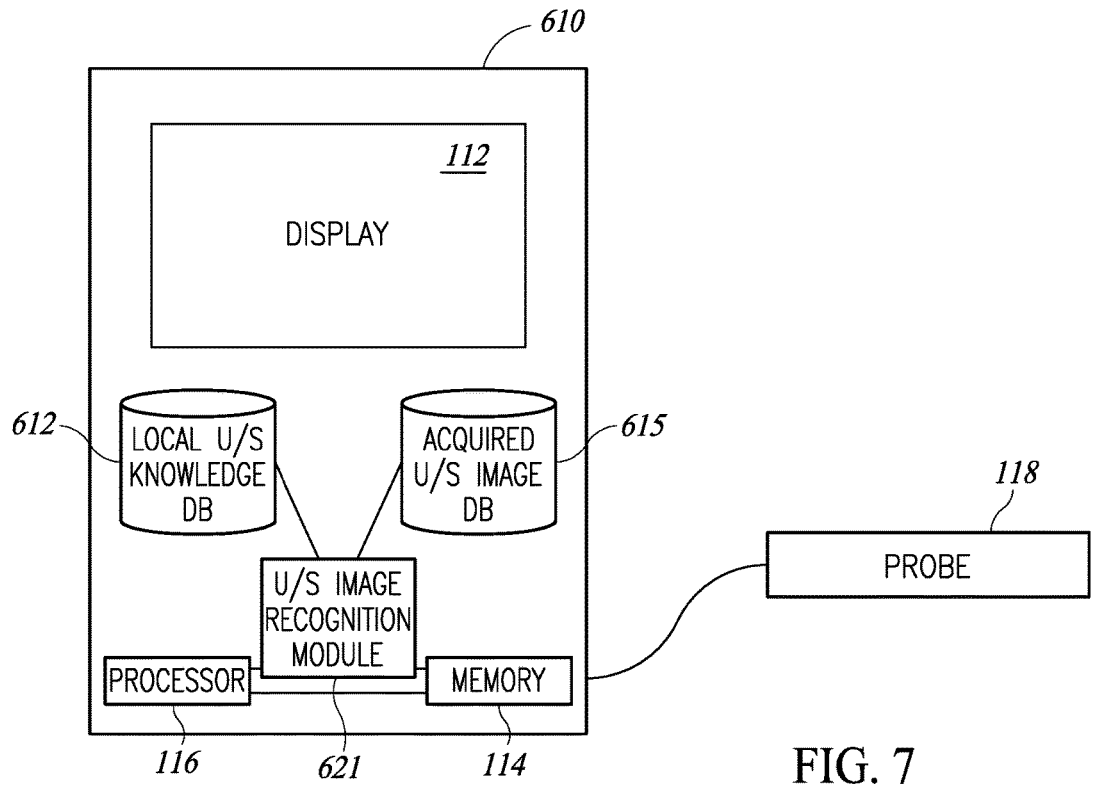
FIG. 7 is a block diagram illustrating an ultrasound imaging device in accordance with one or more embodiments of the disclosure.

With reference to FIG. 7, an ultrasound imaging device 610 may include a display 112, memory 114, one or more processors 116 and an ultrasound image recognition module 621. The ultrasound image recognition module 621 included with the ultrasound imaging device 610 may be essentially the same as the ultrasound image recognition module 120 shown in, and described with respect to, FIG. 1. One difference is that the ultrasound image recognition module 621 (as well as the local ultrasound knowledge database 612) is located within the ultrasound imaging device 610 of FIG. 8, while the ultrasound image recognition module 120 is located remotely with respect to the ultrasound imaging device 110 of FIG. 1.

The ultrasound imaging device 610 may further include an acquired ultrasound image database 615 and/or a local ultrasound image knowledge database 612. The ultrasound imaging device 610 is operatively coupled to an ultrasound probe 118.

The memory 114, processor 116, ultrasound probe 118 and display 112 are described above with respect to the ultrasound imaging device 110 of FIG. 1.

The ultrasound image recognition module 621 may incorporate, for example, a portion or all of the pre-trained cloud-based AI training network 620, including the image knowledge acquired and stored in the image knowledge database 622. That is, the ultrasound imaging devices 610 may download, via a communications network 602, the AI training network 620 and/or the ultrasound image knowledge stored in the ultrasound image knowledge database 622 (which may be stored, for example, in the local ultrasound image knowledge database 612). Accordingly, the image knowledge learned by the AI training network 620 may be applied by the ultrasound image recognition module 621 to process and make determinations regarding the ultrasound images acquired by the ultrasound imaging device 610. Communications network 602 may utilize one or more protocols to communicate via one or more physical networks, including local area networks, wireless networks, dedicated lines, intranets, the Internet, and the like.

The ultrasound images thus acquired by the ultrasound imaging device 610 may be provided to, and processed by, the ultrasound image recognition module 621. The ultrasound image recognition module 621 receives the ultrasound images acquired by the ultrasound imaging device 610, and determines whether one or more of the received ultrasound images represent a clinically desirable view of an organ or other aspect, region or feature of the patient or whether the clinically desirable views indicate normal function or a particular pathology. The ultrasound image recognition module 621 may be implemented by any computationally intelligent system that employs artificial intelligence, drawing from learned knowledge such as contained in a local ultrasound image knowledge database 612, to determine whether received ultrasound images represent a clinically desirable view or whether the clinically desirable views indicate normal function or a particular pathology.

The ultrasound image knowledge database 622 may be similar to, or the same as, the ultrasound image knowledge database 122 shown in FIG. 1. The AI training network 620 is similar to the ultrasound image recognition module 120 shown in FIG. 1, in that the AI training network 620 is trained and develops ultrasound image knowledge (which is stored in the ultrasound image knowledge database 622) for making determinations with respect to ultrasound images acquired by an ultrasound imaging device 610. One difference, however, is that the AI training network 620 is trained, in part, by actual ultrasound images acquired by numerous ultrasound imaging devices 610, which are provided to the AI training network 620 for further training and development of additional or refined ultrasound image knowledge.

Figure 8:
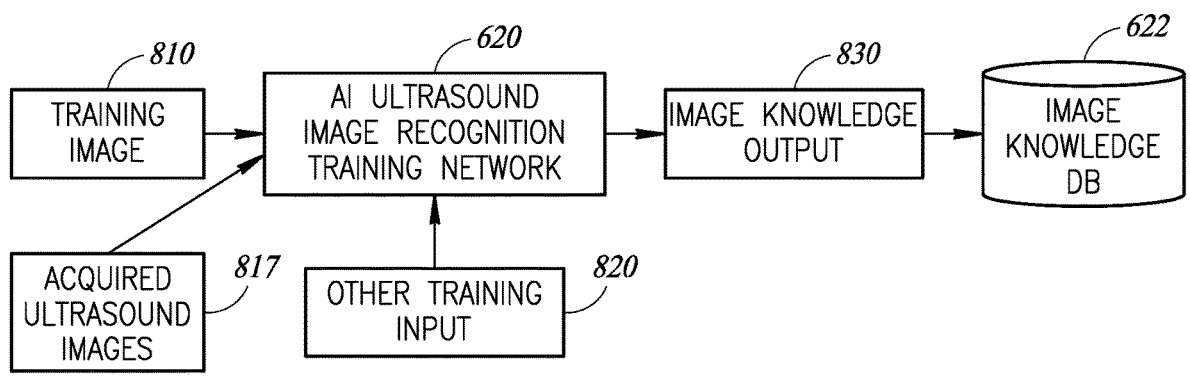
FIG. 8 is a block diagram illustrating training of an artificial intelligence ultrasound image recognition training network in accordance with one or more embodiments of the disclosure.

FIG. 8 is a block diagram illustrating training of the cloud-based AI training network 620, in accordance with one or more embodiments. The AI training network 620 may initially be trained using training images 810. Training images 810 may include any ultrasound image information, and may be the same as or similar to the training images 210 shown in, and described with respect to, FIG. 2. For example, the training images 810 may include a variety of ultrasound image information associated with known views of an organ (such as clinically desirable images of, e.g., suprasternal views of a heart). Further, the training images 810 may be ultrasound images which have been pre-determined (e.g., by a physician) as adequately showing a particular clinically desirable view. Additionally, a wide variety of images with various characteristics representing normal function and/or certain pathologies may be included in the training images 810.

Moreover, the training images 810 may include image information associated with non-clinically desirable views, as discussed above with respect to the training images 210 provided for training the ultrasound image recognition module 120, as shown in FIG. 2. Accordingly, the AI training network 620 may receive, for example, a view of a heart which is not representative of any particular clinically desirable view, but may nonetheless recognize the image as being a view of a heart, and may further recognize the image as being an image somewhere between, for example, a 2-chamber apical view and a 3-chamber apical view. The AI training network 620 may be trained with training images 810 showing a variety of known, but non-clinically desirable, views of a heart (such as views somewhere between the 2-chamber apical and the 3-chamber apical views), and thus may develop knowledge facilitating recognition of such views (e.g., the AI training network 620 may recognize a view as representing a 35° counterclockwise rotation of the probe 118 with respect to the 2-chamber apical view). In accordance with one or more embodiments, feedback is provided to the user regarding recognition (or lack thereof) and identification or interpretation (or lack thereof) of the image captured, as described for example, with respect to FIG. 1 (feedback 103).

Other training input 820 may further be provided to the AI training network 620 for training. The other training input 820 may include, for example, manually-entered input to adjust or otherwise manage the image recognition model developed in the AI training network 620 through the training process.

Using training images 810, the AI training network 620 may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

As discussed previously with respect to FIG. 3, the back-propagation learning algorithm is a common method of training artificial neural networks (and may be employed, for example, with the artificial neural network 300 shown in FIG. 3, which may be utilized or implemented by the AI training network 620).

As a result of the training, the AI training network 620 may learn to modify its behavior in response to the training images 810, and obtain or generate ultrasound image knowledge 830. The ultrasound image knowledge 830 may represent any information upon which an artificial intelligence network (e.g., the AI training network 620 and/or the ultrasound image recognition module 621) may determine to be an appropriate response to new data or situations. In particular, the ultrasound image knowledge 830 represents relationships between ultrasound images and one or more views of an organ and normal versus pathological conditions of an organ (e.g., one or more functions that describe one or more views of an organ based on ultrasound image parameters, coefficients, weighting information, parameters associated with the example neural network shown in FIG. 3 or any such variable). The ultrasound image knowledge 830 may be stored in the ultrasound image knowledge database 622.

Once the AI training network 620 is sufficiently trained based on the initial training images 810, the ultrasound imaging devices 610 may download (e.g., as indicated by reference numeral 603) the trained AI training network 620 and/or the image knowledge developed by the AI training network 620 and stored in the ultrasound image knowledge database 622, via the communications network 602. That is, the ultrasound image recognition module 621 in the ultrasound imaging devices 610 may include one or more portions of, or may be a complete copy of, the already trained AI training network 620, and the local ultrasound image knowledge database 612 within the ultrasound imaging devices 610 may be provided with some or all of the ultrasound image knowledge stored in the ultrasound image knowledge database 622.

The ultrasound imaging devices 610 are thus equipped to acquire unknown ultrasound images during normal operational use, and to determine (e.g., by the ultrasound image recognition module 621) whether the acquired ultrasound images represent a clinically desirable view of a patient or whether the clinically desirable views indicate normal function or a particular pathology.

Images acquired by the ultrasound imaging devices 610 during normal operational use (e.g., acquired diagnostic images 817 of a patient) may be stored in the acquired ultrasound image database 615, and further may be provided to the AI training network 620 (shown in FIG. 6, for example, at reference numeral 601) as additional training inputs, thereby further training the AI training network 620. Such acquired ultrasound images 817 may be images directly acquired by the ultrasound imaging devices 610 and/or may be images that have been verified, modified and/or otherwise clinically determined for use as training data for further training the AI training network 620. For example, the acquired ultrasound images 817 may include images obtained by an ultrasound imaging device 610, and which were not correctly determined by the local ultrasound image recognition module 621. For example, the ultrasound image recognition module 621 may determine that a particular image does not represent a clinically desirable view (e.g., a suprasternal view of heart); however, that same image may in fact represent the clinically desirable view. For example, a physician or other such expert may, upon independent review of the ultrasound image, determine that the image does in fact show a clinically sufficient suprasternal view of heart, but the ultrasound image recognition module 621 did not make same determination, thus reflecting that the ultrasound image recognition module 621 may be further optimized to determine or recognize the image correctly. In such a case, the acquired ultrasound image may be modified, labeled or otherwise associated with training data indicating that the acquired image represents a clinically desirable view (e.g., a suprasternal view of a heart), and may thus be provided as an acquired ultrasound image 817 for further training the AI training network 620, which in turn is used to update the ultrasound image recognition module 621.

Ultrasound images obtained by the ultrasound imaging devices 610 may be stored in the acquired ultrasound image database 615 and/or may be modified to include training information (e.g., indicating any known characteristics about the image, such as that the image represents or does not represent a particular clinically desirable view, normal function or known pathology) and then stored in the acquired ultrasound image database 615. Accordingly, acquired ultrasound images 817, having training information indicating one or more known characteristics about the acquired ultrasound images 817, may be provided to the AI training network 620 for further training and for further development and/or refinement of ultrasound image knowledge 830.

The acquired ultrasound images 817 used for further training the AI training network 620 may be received directly from the ultrasound imaging devices 610 (e.g., by uploading images stored in the acquired image database 615, via communications network 602, to the AI training network 620) and/or from one or more user computer devices 630. For example, a physician may download ultrasound images from the ultrasound imaging devices 610 to a user computer device 630, and further may modify, label, or otherwise append training data to the ultrasound images indicating one or more known characteristics associated with the ultrasound images. The user computer device 630 may thus be utilized to transmit the acquired ultrasound images 817 (which may include, for example, the training data indicating one or more known characteristics) to the AI training network 620 for further training. User computer device 630 may also, or alternatively, be used to receive updated knowledge from the AI training network 620, which it may communicate to any associated ultrasound imaging device 610.

The acquired ultrasound images 817 are thus training images used to further train the AI training network 620. That is, the initial set of training images 810 are used to initially train the AI training network 620, and the acquired ultrasound images 817 are provided to further train the AI training network 620 after one or more ultrasound imaging devices 610 have been deployed and have acquired ultrasound images which may provide training value. The training images 810, as well as the acquired ultrasound images 817, include the same type of information, i.e., ultrasound image information and associated training labels.

The training images 810 and/or the acquired ultrasound images 817 for training the AI training network 620 may include a sequence of images (e.g., a video clip having a sequence of successively-acquired image frames). For example, a clip may include a sequence of images indicating a dynamic phenomenon such as heart motion/contractility. Such a clip may be provided to the AI training network 620 as initial training images 810 and/or as acquired ultrasound images 817 for further training the AI training network 620.

Based on the training images 810, the AI training network 620 may learn to modify its behavior, and may apply knowledge contained in the image knowledge database 622 to alter the manner in which it makes determinations with respect to new inputs, such as, for example, acquired ultrasound image information 817 received from the ultrasound imaging devices 610. The acquired ultrasound images 817 may be provided to the AI training network 620 via the communications network 602, and thus may be used as additional training input to further train the AI training network 620, and to generate further developed image knowledge 830, which may be stored in the image knowledge database 622.

An artificial neural network (e.g., the artificial neural network 300, shown in FIG. 3) may be implemented by the AI training network 620 and/or the ultrasound image recognition module 621, in accordance with one or more embodiments.

As discussed above, the artificial neural network 300 shown in FIG. 3 includes three layers: an input layer 310 including input neurons $i_1$ through $i_3$, a hidden layer 320 including hidden layer neurons $h_1$ through $h_4$, and an output layer 330 including output neurons $f_1$ and $f_2$. While the neural network 300 of FIG. 3 is shown having three layers, it should be readily appreciated that additional layers may be included in the neural network 300 as desired to achieve optimal training and performance of the AI training network 620 and/or the ultrasound image recognition module 621. Similarly, the neurons in each layer are shown for exemplary purposes, and it should be readily understood that each layer may include more, even significantly more, neurons than shown in FIG. 3.

The neural network 300 may be trained (e.g., in an embodiment where the AI training network 620 is a neural network 300) by providing training images 810 and/or acquired ultrasound images 817 to the input layer 310. As described with respect to FIG. 8, the training images 810 (as well as the acquired ultrasound images 817, provided as training input to the AI training network 620) may include ultrasound image information having a wide variety of known characteristics, including, for example, various organ views, normal function, various pathologies, various image qualities or characteristics, various imaging angles, and so on. Through training, the neural network 300 may generate and/or modify the hidden layer 320, which represents weighted connections mapping the training images 810 and/or acquired ultrasound images 817 provided at the input layer 310 to known output information at the output layer 330 (e.g., classification of an image as a subcostal view of a heart, a suprasternal view, etc.). Relationships between neurons of the input layer 310, hidden layer 320 and output layer 330, formed through the training process and which may include weight connection relationships, are generally referred to herein as "ultrasound image knowledge," and may be stored, for example, in the ultrasound image knowledge database 622.

Once the neural network 300 has been sufficiently trained, the neural network 300 may be provided to the ultrasound imaging devices 610, and implemented, for example, by ultrasound image recognition module 621. As such, the neural network 300 may receive non-training ultrasound images at the input layer 310 (i.e., ultrasound images taken of a patient utilizing the ultrasound imaging device 610). Utilizing ultrasound image knowledge stored in the ultrasound image knowledge database 622 (which may be provided to and stored in the local ultrasound image knowledge database 612, and which may include, for example, weighted connection information between neurons of the neural network 300), the neural network 300 may make determinations about the received ultrasound image information at the output layer 330. For example, the neural network 300 may determine whether the received ultrasound images represent one or more clinically desirable views of an organ.

Thus, the cloud-based AI training network 620 is initially trained in order to develop a network and/or image knowledge sufficient to implement in an ultrasound image recognition module 621 in the ultrasound imaging devices 610. The cloud-based AI training network 620 then continues to be further trained based on the acquired ultrasound images 817, which are acquired by ultrasound devices 610 and provided to the AI training network 620 via the communications network 602 (shown in FIG. 6, for example, at reference numeral 601). As a result of the continued training of the AI training network 620, the AI training network 620 continues to develop, refine or otherwise generate additional ultrasound image knowledge, which is stored in the ultrasound image knowledge database 622. The ultrasound imaging devices 610 may thus periodically receive updated ultrasound image knowledge stored in the ultrasound image knowledge database 622 (shown in FIG. 6, for example, at reference numeral 603), either through updates that are automatically downloaded per a predetermined schedule, or at a particular time desired or requested by a user, or automatically when the database has received a certain threshold number of additional images that has resulted in the network being further trained since the imaging device (s) were last updated.

The neural network 300 of FIG. 3 is provided as just one example, among various possible implementations, of an AI training network 620 and/or an ultrasound image recognition module 621 that employs artificial intelligence to make determinations with respect to received ultrasound image information. For example, the AI training network 620 and/or the ultrasound image recognition module 621 may implement any of neural network, deep learning, convolutional neural network, and Bayesian program learning techniques to make determinations with respect to received ultrasound images of a patient.

Moreover, the AI training network 620 may be trained, utilizing a variety of training images 810 and/or acquired ultrasound images 817 (and further may be trained utilizing a variety of sequences of training images 810 and/or acquired ultrasound images 817) to make a variety of determinations relating to received ultrasound image information. For example, the AI training network 620 may be trained or otherwise configured to determine whether a received ultrasound image represents one or more clinically standard or desirable views or whether the clinically desirable views indicate normal function or a particular pathology. Further, the AI training network 620 may be trained to determine whether a received ultrasound image represents a non-clinically desirable view (and may recognize such non-clinically desirable view as a particular view or angle of a particular organ or other tissue within a patient), and may further determine based on a sequence of received ultrasound images whether the images are approaching or moving away from a clinically desirable view of an organ.

By downloading the AI training network 620 and/or the ultrasound image knowledge developed by the AI training network 620 and stored in the ultrasound image knowledge database 622, the ultrasound image recognition module 621 and local ultrasound image knowledge database 612 in the ultrasound imaging devices 610 may include all of the features and functionality described herein with respect to the trained AI training network 620 and the ultrasound image knowledge database 622.

For example, as discussed above, the AI training network 620 may be trained with training images 810 and/or acquired ultrasound images 817 showing a variety of known, but non-clinically desirable, views of an organ or other structure in a patient, and thus the ultrasound image recognition module 621 in the ultrasound devices 610 may recognize such views. Further, the AI training network 620 may be trained with one or more sequences of recognized, but non-clinically standard or desirable views, and the AI training network 620 may be trained to recognize a sequence of or progression of such non-clinically desirable views toward and/or away from a clinically desirable view (e.g., the training images 810 may include a sequence of ultrasound images representing rotation of the probe 118 from the 2-chamber apical view toward and/or away from the 3-chamber apical view). The AI training network 620 may thus be trained (and the ultrasound image recognition module 621 in the ultrasound imaging devices 610 may thus be implemented) to recognize that received ultrasound images, while not being representative of a particular clinically desired view, may be getting successively closer to (or moving away from) the clinically desired view.

Further, the AI training network 620 may be trained such that, when implemented as the ultrasound image recognition module 621 in the ultrasound imaging devices 610, the ultrasound image recognition module 621 may determine whether received ultrasound images represent any of a plurality of clinically desirable views of an organ. Such clinically desirable views of an organ may include, for example, suprasternal, subcostal, short- and long-axis parasternal, 2-chamber apical, 3-chamber apical, 4-chamber apical and 5-chamber apical views of a heart.

While FIG. 6 illustrates an ultrasound data information system 600 including a cloud-based ultrasound image recognition AI training network 620, in one or more alternative embodiments the ultrasound image recognition AI training network 620 may be included within one or more of the ultrasound devices 610. Accordingly, the AI training network 620 within an ultrasound imaging device 610 may be trained as described above (and shown, for example, in FIG. 8) based on the initial training images 810, and further may be trained based on acquired ultrasound images 817 which are acquired by the ultrasound imaging device 610 and further have been labeled and/or modified in some way as to provide training information. For example, an ultrasound image acquired by an ultrasound imaging device 610 may be determined by the ultrasound image recognition module 621 and/or the AI training network 620 as not representing a desirable clinical view of a particular organ, such as a heart. An ultrasound technician operating the ultrasound imaging device 610 may know, for example, that the acquired image does in fact represent the clinically desirable view; however, the patient's heart has an atypical anatomy and thus the ultrasound image recognition module 621 and/or the AI training network 620 does not correctly recognize the image as being a clinically desirable view. In such a case, the ultrasound technician may label the acquired image as being the clinically desirable view (e.g., by pressing a corresponding button on the ultrasound imaging device 610, by storing the acquired image in the acquired ultrasound image database 615 for labeling by a physician or other trained expert utilizing the ultrasound imaging device 610 and/or a user computer device 630, or the like). Once labeled as properly representing the clinically desirable view, the image is provided as training input (e.g., acquired ultrasound image 817) to further train the AI training network 620 and/or the ultrasound image recognition module 621 within the ultrasound imaging device 610. Thus, an ultrasound imaging device 610 may include the ability to self-train its internal ultrasound image recognition module 621 based on images acquired by the ultrasound image device 610.

Further, there may be other circumstances in which multiple organizations (e.g., hospitals or clinics) or groups of users of ultrasound imaging devices 610 (e.g., trade associations or informal groups) may each have their own AI training network (e.g., a central AI training network 620, or a separate, organization or group AI training network for providing updated image knowledge, based on ultrasound images acquired by ultrasound imaging devices 610 within the organization or group) and/or knowledge database for their organization or group, with updates being generated from ultrasound images acquired by ultrasound imaging devices 610 in the organization or group.

Figure 9:
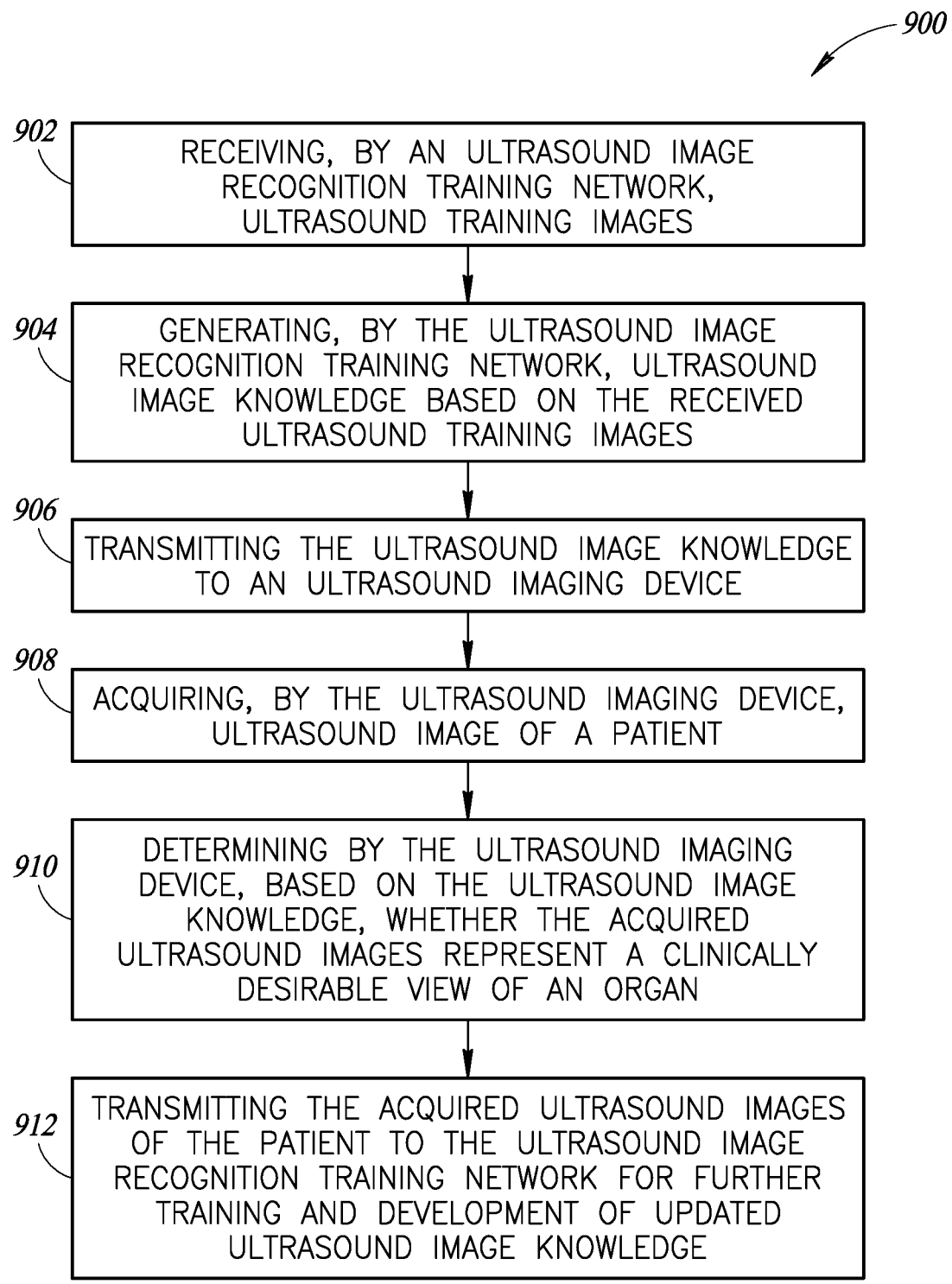
FIG. 9 is a flowchart illustrating an ultrasound image recognition method in accordance with one or more embodiments of the disclosure.

FIG. 9 is a flowchart illustrating a method 900, in accordance with one or more embodiments. At block 902, the method 900 includes receiving, by an ultrasound image recognition training network (e.g., the AI training network 620), ultrasound training images 810.

At block 904, the method 900 includes generating, by the ultrasound image recognition training network, ultrasound image knowledge 830 based on the received ultrasound training images 810. The ultrasound image knowledge 830 may be stored, for example, in the ultrasound image knowledge database 622.

At block 906, the method 900 includes transmitting the ultrasound image knowledge 830 to an ultrasound imaging device 610. The ultrasound imaging devices 610 may periodically poll the AI training network 620 for updated knowledge, and the ultrasound image knowledge 830 may be transmitted in response to the polling. Additionally or alternatively, the AI training network 620 may periodically push updated ultrasound image knowledge 830 to the ultrasound imaging devices 610. In one or more embodiments, one or more of the ultrasound imaging devices 610 and/or user computer devices 630 may receive the updated ultrasound image knowledge 830 and then distribute the updated ultrasound image knowledge 830 to one or more other ultrasound imaging devices 610 (e.g., via a peer-to-peer or other local network). For example, one or more user computer devices 630 may be located within a clinical setting, such as a hospital, and may receive and provide updated ultrasound image knowledge 830 to multiple ultrasound imaging devices 610 located within the same setting.

The ultrasound image knowledge 830 may be transmitted to the ultrasound imaging device 610, for example, directly from the ultrasound image knowledge database 622 or from the AI training network 620. Alternatively, the ultrasound image knowledge 830 may be provided to a user computer device 630, which then transmits the ultrasound image knowledge 830 to one or more ultrasound imaging devices 610. The transmitted ultrasound image knowledge may be stored in the local ultrasound image knowledge database 612, which may be contained within the ultrasound imaging device 610.

At block 908, the method 900 further includes acquiring, by the ultrasound imaging device 610, ultrasound images of a patient. At block 910, the method 900 includes determining by the ultrasound imaging device 610 (e.g., utilizing the ultrasound image recognition module 621) whether the acquired ultrasound images represent a clinically desirable view of an organ. The determining may be performed, for example, based on the ultrasound image knowledge 830.

At block 912, the method 900 includes transmitting the acquired ultrasound images of the patient to the ultrasound image recognition training network for further training. The transmitted acquired ultrasound images of the patient may include training data indicating one or more known characteristics associated with the acquired ultrasound images.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultrasound system, comprising:
an ultrasound imaging device including a handheld probe configured to acquire ultrasound images of a patient while the handheld probe is moving; and
an ultrasound image recognition module configured to:
receive the acquired ultrasound images from the ultrasound imaging device;
automatically determine, by implementing a trained neural network continuously while the handheld probe is moving during examination of the patient, whether the received ultrasound images represent a clinically desirable view of an organ, wherein the clinically desirable view of the organ includes at least one of suprasternal, subcostal, short axis parasternal, long axis parasternal, 2-chamber apical, 3-chamber apical, 4-chamber apical and 5-chamber apical views of a heart; and
automatically determine a specific user motion of the handheld probe for acquiring the clinically desirable view of the organ; and
provide an indication to the user of the specific user motion, the indication including at least one of an indication of a user rotation of the handheld probe or an indication of a user translation of the handheld probe in a specific direction.

2. The ultrasound system of claim 1, wherein the trained neural network includes at least one of a deep learning network or a convolutional neural network.

3. The ultrasound system of claim 1, the ultrasound imaging device including a user interface operable to receive a selection of one of a plurality of clinically desirable views of the organ, wherein the ultrasound image recognition module is configured to determine whether the received ultrasound images represent the selected clinically desirable view of the organ.

4. The ultrasound system of claim 1, wherein the ultrasound image recognition module is operable to automatically determine whether the received ultrasound images represent at least one of a plurality of clinically desirable views of the organ.

5. The ultrasound system of claim 1, wherein the ultrasound image recognition module is further configured to provide a feedback signal to the ultrasound imaging device, in response to determining whether the received ultrasound images represent the clinically desirable view of the organ.

6. The ultrasound system of claim 5, wherein the feedback signal indicates whether a most recently received ultrasound image represents the clinically desirable view of the organ.

7. The ultrasound system of claim 5, wherein the ultrasound image recognition module automatically determines whether the received ultrasound images are sequentially approaching or moving away from the clinically desirable view of the organ, wherein the feedback signal indicates whether the received ultrasound images are sequentially approaching or moving away from the clinically desirable view of the organ.

8. The ultrasound system of claim 5, the ultrasound imaging device including a feedback element, the ultrasound imaging device being configured to activate the feedback element, based on the feedback signal, to provide a feedback effect to a user of the ultrasound imaging device.

9. The ultrasound system of claim 8, wherein the feedback element comprises at least one of a visual, audible or haptic feedback element.

10. The ultrasound system of claim 1, further comprising a non-transitory computer-readable storage medium, wherein the ultrasound imaging device is configured to provide an acquired ultrasound image to the storage medium for storage in response to the ultrasound image recognition module determining that the acquired ultrasound image represents the clinically desirable view of the organ.

11. The ultrasound system of claim 1, wherein the ultrasound image recognition module is operated within the ultrasound imaging device.

12. A method, comprising:
acquiring, by a handheld probe of an ultrasound imaging device, ultrasound images of a patient while the handheld probe is moving;
transmitting the acquired ultrasound images of the patient to an ultrasound image recognition module;
automatically determining, by the ultrasound image recognition module implementing a trained neural network continuously while the handheld probe is moving during examination of the patient, whether the acquired ultrasound images represent a clinically desirable view of an organ wherein the clinically desirable view of the organ includes at least one of suprasternal, subcostal, short axis parasternal, long axis parasternal, 2-chamber apical, 3-chamber apical, 4-chamber apical and 5-chamber apical views of a heart; and
automatically determining a specific user motion of the handheld probe for acquiring the clinically desirable view of the organ; and
providing an indication to the user of the specific user motion, the indication including at least one of a user rotation of the handheld probe or a user translation of the handheld probe in a specific direction.

13. The method of claim 12, wherein
implementing the trained neural network includes implementing at least one of a deep learning network or a convolutional neural network.

14. The method of claim 12, further comprising:
receiving a selection of one of a plurality of clinically desirable views of the organ, wherein the ultrasound image recognition module is configured to determine whether the received ultrasound images represent the selected clinically desirable view of the organ.

15. The method of claim 12, further comprising:
transmitting a feedback signal to the ultrasound imaging device, in response to the determining whether the received ultrasound images represent the clinically desirable view of the organ.

16. The method of claim 15, further comprising:
automatically determining, by the ultrasound image recognition module, whether the received ultrasound images are sequentially approaching or moving away from the clinically desirable view of the organ, wherein the feedback signal indicates whether the received ultrasound images are sequentially approaching or moving away from the clinically desirable view of the organ.

17. The method of claim 15, further comprising:
activating a feedback element in the ultrasound imaging device, based on the feedback signal, to provide a feedback effect to a user of the ultrasound imaging device.

18. The method of claim 12, further comprising:
storing an acquired ultrasound image in a non-transitory computer-readable storage medium in response to the ultrasound image recognition module determining that the acquired ultrasound image represents the clinically desirable view of the organ.

19. An ultrasound data information system, comprising:
an ultrasound image recognition training network stored at least partially on a computer device having one or more processors, the ultrasound image recognition training network including a neural network configured to receive ultrasound training images, and to develop ultrasound image knowledge based on the received ultrasound training images;
an ultrasound imaging device including a handheld probe configured to acquire ultrasound images of a patient while the handheld probe is moving; and
an ultrasound image recognition module, within the ultrasound imaging device, the ultrasound image recognition module being configured to:
receive the ultrasound image knowledge;
receive the acquired ultrasound images from the ultrasound imaging device;
determine, based on the ultrasound image knowledge, continuously while the handheld probe is moving during examination of the patient whether the received ultrasound images represent a clinically desirable view of an organ, wherein the clinically desirable view of the organ includes at least one of suprasternal, subcostal, short axis parasternal, long axis parasternal, 2-chamber apical, 3-chamber apical, 4-chamber apical and 5-chamber apical views of a heart; and
determine a specific user motion of the handheld probe for acquiring the clinically desirable view of the organ; and
provide an indication to the user of the specific user motion, the indication including at least one of an indication of a user rotation of the handheld probe or an indication of a user translation of the handheld probe in a specific direction.

20. The ultrasound data information system of claim 19, wherein the neural network of the ultrasound image recognition training network includes at least one of a deep learning network or a convolutional neural network.

21. The ultrasound data information system of claim 19, wherein the ultrasound image recognition module is operable to determine whether the received ultrasound images represent at least one of a plurality of clinically desirable views of the organ.

22. The ultrasound data information system of claim 19, wherein the ultrasound imaging device is further configured to provide the acquired ultrasound images to the ultrasound image recognition training network for further training the ultrasound image recognition training network and developing updated ultrasound image knowledge.

23. The ultrasound data information system of claim 19, wherein the ultrasound image recognition training network is configured to receive ultrasound training images, the ultrasound training images including initial training images and the ultrasound images acquired by the ultrasound imaging device.

24. The ultrasound data information system of claim 19, wherein the ultrasound image recognition module is configured to determine whether the received ultrasound images are sequentially approaching or moving away from the clinically desirable view of the organ.

25. The ultrasound data information system of claim 19, further comprising:
an ultrasound image knowledge database, communicatively coupled to the ultrasound image recognition training network and configured to store the ultrasound image knowledge; and
a local ultrasound image knowledge database, communicatively coupled to the ultrasound imaging device and configured to store at least a portion of the ultrasound image knowledge.

26. The ultrasound data information system of claim 19, the ultrasound image recognition module being further configured to:
determine, based on the ultrasound image knowledge, whether the received ultrasound images indicate normal function or a particular pathology.

27. A method, comprising:
receiving, by an ultrasound image recognition training network including a neural network, ultrasound training images;
generating, by the ultrasound image recognition training network, ultrasound image knowledge based on the received ultrasound training images;
transmitting the ultrasound image knowledge to an ultrasound imaging device including a handheld probe, the ultrasound imaging device being separate from and located remotely from the ultrasound image recognition training network;
acquiring, by the ultrasound imaging device, ultrasound images of a patient while the handheld probe is moving;
automatically determining, based on the ultrasound image knowledge, continuously while the handheld probe is moving during examination of the patient, whether the acquired ultrasound images represent a clinically desirable view of a structure, wherein the clinically desirable view of the structure includes at least one of suprasternal, subcostal, short axis parasternal, long axis parasternal, 2-chamber apical, 3-chamber apical, 4-chamber apical and 5-chamber apical views of a heart; and
automatically determining a specific user motion of the handheld probe for acquiring the clinically desirable view of the structure; and
providing an indication to the user of the specific user motion, the indication including at least one of a user rotation of the handheld probe or a user translation of the handheld probe in a specific direction.

28. The method of claim 27, further comprising:
transmitting the acquired ultrasound images of the patient to the ultrasound image recognition training network for further training the ultrasound image recognition training network and generating updated ultrasound image knowledge.

29. The method of claim 27, wherein the neural network includes at least one of a deep learning network or a convolutional neural network.

30. The method of claim 28, wherein the transmitted acquired ultrasound images of the patient include training data indicating one or more known characteristics associated with the acquired ultrasound images.

31. The method of claim 27, further comprising:
determining, based on the ultrasound image knowledge, whether the acquired ultrasound images indicate normal function or a particular pathology.

32. The ultrasound system of claim 1, wherein the ultrasound imaging device includes a motion sensor within the handheld probe, and the ultrasound imaging device is configured to determine a position and an orientation of the handheld probe based on an output of the motion sensor.

33. The ultrasound system of claim 32, wherein the ultrasound image recognition module is configured to assist the user to acquire the clinically desirable view of the organ by providing an indication of the specific user motion of the handheld probe based on the position and the orientation of the handheld probe.

34. The ultrasound system of claim 32, wherein the ultrasound imaging device is configured to:
determine that an ultrasound image acquired at the determined position and orientation of the handheld probe represents a non-clinically desirable view of the organ; and
provide an indication of the specific user motion of the handheld probe to acquire the clinically desirable view of the organ.

35. The ultrasound system of claim 1, wherein the ultrasound image recognition module is configured to assist the user to acquire the clinically desirable view of the organ by providing an indication of the specific user motion of the handheld probe in response to determining that the received ultrasound images do not represent the clinically desirable view of the organ.

* * * * *